United States Patent [19]

Ammermann et al.

[11] 4,272,551
[45] Jun. 9, 1981

[54] N-SULFENYLATED FORMANILIDES USEFUL AS FUNGICIDES AND BACTERICIDES

[75] Inventors: Eberhard Ammermann, Ludwigshafen; Sabine Thym, Heidelberg; Ernst-Heinrich Pommer, Limburgerhof, all of Fed. Rep. of Germany

[73] Assignee: BASF Aktiengesellschaft, Fed. Rep. of Germany

[21] Appl. No.: 71,550

[22] Filed: Aug. 30, 1979

[30] Foreign Application Priority Data

Sep. 6, 1978 [DE] Fed. Rep. of Germany ....... 2838750

[51] Int. Cl.³ .................. A01N 37/18; A01N 37/34; A01N 37/00; C07C 97/16
[52] U.S. Cl. .................. 424/324; 260/465 R; 260/465 G; 424/304; 424/306; 564/102
[58] Field of Search .................. 424/304, 324, 306; 260/562 R, 465 R, 465 G

[56] References Cited

U.S. PATENT DOCUMENTS

| 3,576,872 | 4/1971 | Singhal | 260/562 R |
|---|---|---|---|
| 3,697,571 | 10/1972 | Brown | 424/298 |
| 3,972,889 | 8/1976 | Brown et al. | 424/298 |
| 3,980,693 | 9/1976 | Kühle et al. | 424/304 |
| 4,098,810 | 7/1978 | Thym et al. | 424/298 |
| 4,117,150 | 9/1978 | Pommer et al. | 424/285 |

FOREIGN PATENT DOCUMENTS 2611902 10/1977 Fed. Rep. of Germany .
2703023 7/1978 Fed. Rep. of Germany .

OTHER PUBLICATIONS

Chem. Week, Jun. 21, 1972, pp. 46 and 63.

*Primary Examiner*—Douglas W. Robinson
*Attorney, Agent, or Firm*—Keil & Witherspoon

[57] ABSTRACT

New N-sulfenylated formanilides, a process for their manufacture, their use as fungicides, fungicides containing these compounds, fungicidal mixtures containing these active ingredients, a process for producing such fungicidal mixtures, and a process for combating injurious fungi with these fungicides or with fungicidal mixtures containing these compounds.

3 Claims, No Drawings

N-SULFENYLATED FORMANILIDES USEFUL AS FUNGICIDES AND BACTERICIDES

The present invention relates to new and valuable N-sulfenylated formanilides, a process for their manufacture, their use as fungicides, fungicides containing these compounds, fungicidal mixtures containing these active ingredients, a process for producing such fungicidal mixtures, and a process for combating injurious fungi with these fungicides or with fungicidal mixtures containing these compounds.

The use of N-sulfenylated imides as fungicides has been disclosed (Chemical Week, June 21, 1972, pp. 46 and 63). However, their fungicidal action is not completely satisfactory.

We have now found that N-sulfenylated formanilides of the formula

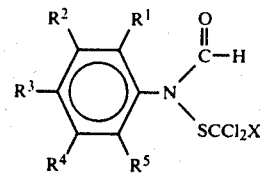

where X denotes fluorine or chlorine, and $R^1$, $R^2$, $R^3$, $R^4$ and $R^5$ are identical or different and each denotes hydrogen, halogen, nitro, linear or branched, unsubstituted or halogen-substituted alkyl or alkoxy of 1 to 4 carbon atoms, or —CN or —$COR^6$, $R^6$ denoting linear or branched alkoxy of 1 to 6 carbon atoms or dialkylamino, the alkyls being linear or branched and of 1 to 4 carbon atoms, or forming, together with the nitrogen atom whose substituents they are, a ring, or $R^6$ denoting N-alkyl-N-arylamino, alkyl being of from 1 to 4 carbon atoms and aryl being unsubstituted or substituted by halogen or alkyl, have a good fungicidal action which is superior to that of prior art N-sulfenylated imides.

Examples of meanings for $R^1$, $R^2$, $R^3$, $R^4$ and $R^5$ are hydrogen, halogen, e.g., fluorine, chlorine, bromine and iodine; linear or branched, unsubstituted or halogen-substituted alkyl or alkoxy of from 1 to 4 carbon atoms, e.g., methyl, ethyl, propyl, isopropyl, n-butyl, isobutyl, sec-butyl, tert-butyl, methoxy, ethoxy, tert-butoxy, trifluoromethyl, and tetrafluoro/ethoxy; nitro, or —CN or —$COR^6$, $R^6$ denoting linear or branched alkoxy of 1 to 6 carbon atoms, e.g., methoxy, ethoxy, propoxy, isopropoxy, n-butoxy, tert-butoxy, and hexoxy, or dialkylamino, the alkyls being linear or branched and of 1 to 4 carbon atoms, e.g., N,N-dimethylamino, N,N-diisopropylamino, N-methylamino, or N-tert-butylamino, or forming, together with the nitrogen atom, a ring which may or may not also contain hetero atoms, e.g., piperidine or morpholine, or $R^6$ denotes N-alkyl-N-arylamino which may or may not be substituted in the aryl ring by alkyl or halogen, e.g., N-methyl-N-(4-chlorophenyl)-amino or N-ethyl-N-(3-isopropylphenyl)-amino.

The new N-sulfenylated formanilides may for instance be prepared by reacting a formanilide of the formula

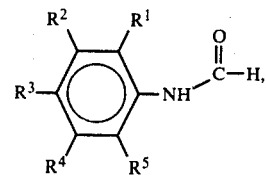

where $R^1$, $R^2$, $R^3$, $R^4$ and $R^5$ have the above meanings, with a compound of the formula $ClSCCl_2X$, where X denotes chlorine or fluorine, at from 0° to 100° C. in the presence of an acid binder and, if desired, in an inert organic solvent.

The formanilides required as starting materials are known (Beilstein, Handbuch der organischen Chemie, 12, 230, 599, 604, 611, 919), or they are manufactured by reaction of anilines with formic acid (cf. Houben-Weyl, 8, 654, 1952, Stuttgart). For instance, 2-fluoroformanilide is obtained by reaction of 2-fluoroaniline with formic acid as follows. 75.5 ml of formic acid is added to 55.5 g of 2-fluoroaniline and the mixture is stirred for 3 hours at reflux temperature. After the reaction mixture has cooled, it is stirred into 1 liter of ice water and the precipitate is filtered off and dried. There is obtained 49 g of 2-fluoroformanilide of melting point 48°–50° C.

Examples of suitable diluents in the manufacture of the N-sulfenylated formanilides are hydrocarbons, e.g., n-pentane, n-hexane, petroleum ether, cyclohexane, benzene, toluene, and xylene, or other organic solvents, e.g., chlorobenzene, diethyl ether, tetrahydrofuran, dioxane, chloroform, methylene chloride, tetrachloroethane, acetone, diisopropyl ketone, sulfolane, dimethyl sulfoxide and dimethylformamide, or mixtures thereof. The diluent is advantageously used in an amount of from 100 to 2,000, preferably from 100 to 1,000, wt%, based on the starting materials.

Acid binders which may be used are alkali metal hydrides or carbonates, e.g., sodium hydride, sodium carbonate, and potassium carbonate, or tertiary amines, e.g., triethtylamine, N,N-dimethylcyclohexylamine, N-methylpiperidine, N,N-dimethylaniline, and pyridine. The acid binder is used for example in stoichiometric amounts or in an excess, e.g., an up to 50% excess. The sulfenyl halide of the formula $ClSCCl_2X$, e.g., trichloromethylsulfenyl chloride or fluorodichloromethylsulfenyl chloride, is added for instance in a stoichiometric amount with respect to, or in an excess of up to 50% over, the formanilide.

The reaction is carried out at for instance from 0° to 100° C., preferably from 0° to 60° C., during a period of from 30 minutes to 120 hours, preferably from 1 hour to 20 hours, at atmospheric or superatmospheric pressure, and continuously or batchwise.

In a preferred embodiment of the manufacturing process, a formanilide (if desired, substituted in any manner) and trichloromethylsulfenyl chloride or fluorodichloromethylsulfenyl chloride are mixed in an equimolar ratio in any order in a diluent. The equimolar amount of the acid binder is then added and the reaction carried out at from 0° to 60° C. for from 1 to 20 hours.

To isolate the new compounds, the reaction mixture is washed with water to remove the salts which have formed. After the reaction product has been concentrated in vacuo it is generally pure enough; however, it may also be further purified by the conventional methods of recrystallization, extraction or chromatography.

The following example illustrates the preparation of the new compounds.

EXAMPLE 1 (compound no. 3)

The product was characterized by infrared spectroscopy, $^1$H-nuclear resonance spectroscopy and elemental analysis.

The following compounds were prepared analogously.

| No. | $R^1$ | $R^2$ | $R^3$ | $R^4$ | $R^5$ | X | m.p. [°C] or $n_D^{20}$ |
|---|---|---|---|---|---|---|---|
| 1 | H | H | H | H | H | Cl | 64–66 |
| 2 | H | H | H | H | H | F | 50–55 |
| 3 | F | H | H | H | H | Cl | 43–46 |
| 4 | F | H | H | H | H | F | oil |
| 5 | H | H | F | H | H | Cl | oil |
| 6 | H | H | F | H | H | F | 51–54 |
| 7 | Cl | H | H | H | H | Cl | 56–58 |
| 8 | Cl | H | H | H | H | F | 1.5658 |
| 9 | H | Cl | H | H | H | Cl | 68–70 |
| 10 | H | Cl | H | H | H | F | 1.5679 |
| 11 | H | H | Cl | H | H | Cl | 76–78 |
| 12 | H | H | Cl | H | H | F | 50 |
| 13 | H | Cl | H | Cl | H | Cl | 85–90 |
| 14 | H | Cl | H | Cl | H | F | 64 |
| 15 | Cl | H | Cl | Cl | H | Cl | 1.5788 |
| 16 | Cl | H | Cl | Cl | H | F | 1.5753 |
| 17 | Br | H | Br | H | H | Cl | 1.6024 |
| 18 | Br | H | Br | H | H | F | wax |
| 19 | H | I | H | H | H | Cl | 62–65 |
| 20 | H | I | H | H | H | F | 1.5610 |
| 21 | $CH_3$ | H | Cl | H | H | Cl | 1.4990 |
| 22 | $CH_3$ | H | Cl | H | H | F | 1.5575 |
| 23 | $CH_3$ | H | H | H | H | Cl | 58–60 |
| 24 | $CH_3$ | H | H | H | H | F | 1.5580 |
| 25 | $CH_3$ | H | H | H | $CH_3$ | Cl | 1.5800 |
| 26 | $CH_3$ | H | H | H | $CH_3$ | F | 1.5534 |
| 27 | H | $NO_2$ | H | H | H | Cl | 1.5960 |
| 28 | H | $NO_2$ | H | H | H | F | 1.5732 |
| 29 | H | $CF_3$ | H | H | H | Cl | 75–76 |
| 30 | H | $CF_3$ | H | H | H | F | 61–63 |
| 31 | H | H | $CF_3$ | H | H | Cl | 42 |
| 32 | H | H | $CF_3$ | H | H | F | 42 |
| 33 | H | $CF_3$ | H | $CF_3$ | H | Cl | 1.4908 |
| 34 | H | $CF_3$ | H | $CF_3$ | H | F | 1.4739 |
| 35 | H | $OC_2HF_4$ | H | H | H | Cl | 1.5070 |
| 36 | H | $OC_2HF_4$ | H | H | H | F | 1.4982 |
| 37 | H | $i$-$C_3H_7$ | H | H | H | Cl | 1.5610 |
| 38 | H | $i$-$C_3H_7$ | H | H | H | F | 1.5359 |
| 39 | Cl | H | H | $CF_3$ | H | Cl | 1.532 |
| 40 | Cl | H | H | $CF_3$ | H | F | 1.519 |
| 41 | $OCH_3$ | H | Cl | H | H | Cl | 117–122 |
| 42 | $OCH_3$ | H | Cl | H | H | F | 85–88 |
| 43 | H | H | $CO_2C_2H_5$ | H | H | Cl | wax |
| 44 | H | H | $CO_2C_2H_5$ | H | H | F | 1.5378 |
| 45 | F | H | H | H | F | Cl | 64–65 |
| 46 | F | H | H | H | F | F | 50–52 |
| 47 | H | Cl | F | H | H | Cl | 59–61 |
| 48 | H | Cl | F | H | H | F | oil |
| 49 | H | $CO_2$—$i$-$C_3H_7$ | H | $CO_2$—$i$-$C_3H_7$ | H | Cl | 78–80 |
| 50 | H | $CO_2$—$i$-$C_3H_7$ | H | $CO_2$—$i$-$C_3H_7$ | H | F | 1.5088 |
| 51 | H | H | $CH_3$ | H | H | F | 56 |

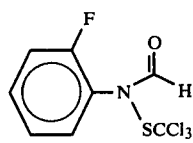

At room temperature, 39 g of trichloromethylsulfenyl chloride was added to 19.5 g of 2-fluoroformanilide in 200 ml of cyclohexane. While stirring, 22 ml of triethylamine was dripped in, the temperature rising to 40° C. After the reaction mixture had been stirred overnight at room temperature, it was washed 3 times with water, dried and concentrated.

The residue was recrystallized from isopropanol and there was obtained 20 g of white crystals of N-(trichloromethylsulfenyl)-2-fluoroformanilide, m.p.: 43°–46° C.

The new active ingredients are predominantly suitable for combating phytopathogenic soil fungi, e.g., Pythium, Aphanomyces and Fusarium species, which may cause emergence and seedling diseases for instance in leguminosae, lettuce, beets, cotton and other crop plants; they are also suitable for combating molds, e.g., Aspergillus and Penicillium species, which inflict heavy attack on flower bulbs and may cause putrefaction.

In addition, the new compounds are suitable for protecting various materials against degradation or destruction by bacteria and fungi. Examples of materials which can be preserved or microbicidally finished with the new active ingredients are paints, sealants, plastics, wood and wood-base materials; further, the compounds may also be used as antislime agents in the paper industry.

The following microorganisms for instance may be combated with the compounds according to the invention for the protection of materials:

*Chaetomium globosum, Aspergillus terreus, Aspergillus niger,*
*Aspergillus versicolor, Penicillium glaucum, Pullularia pullulans,*
*Sclerophoma pityophila, Phoma violacea, Staphylococcus aureus,*
*Escherichia coli, Pseudomonas aeruginosa* both Nostoc spec.,
*Chlorella vulgaris* and *Scenedesmus quadricauda.*

The fungicidal agents contain from 0.1 to 95, preferably from 0.5 to 90, wt% of active ingredient. Depending on the effect desired, application rates are from 0.001 to 3 kg of active ingredient per hectare and more, but preferably from 0.01 to 1 kg of active ingredient per hectare.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as bark meal, wood meal, and nutshell meal, cellulosic powders, etc.

When the active ingredients are used for protecting materials, e.g., as fungicides in paints, application rates are from 0.5 to 5% of active ingredient, based on the total weight of the paints to be preserved. The new active ingredients may also be used as fungicidally effective components of oily wood preservatives for the protection of wood against wood-destroying or wood-discoloring fungi. The wood is treated with these agents, e.g., by impregnation or coating.

The active ingredients may also be mixed with other, prior art, fungicides. In many cases, the spectrum of fungicidal action is broadened; with a number of these fungicide mixtures synergistic effects also occur, i.e., the fungicidal action of the mixture is greater than the sum of the action of its individual components.

The following list of fungicides with which the compounds according to the invention can be combined is intended to illustrate possible combinations, but the invention is in no way limited to these. Examples of fungicides with which the new N-sulfenylated formalides can be combined are as follows:

ferric dimethyldithiocarbamate
zinc dimethyldithiocarbamate
manganese ethylene bisdithiocarbamate
zinc ethylenebisthiocarbamate
tetramethylthiuram disulfide
3,5-dimethyl-1,3,5-2H-tetrahydrothiadiazine-2-thione
manganese-zinc ethylenediamine-bisdithiocarbamate
zinc-(N,N'-propylene-bisdithiocarbamate)
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
2,4,5-trichlorophenol
pentachlorophenol
barium salt of pentachlorophenol
pentachlorophenyl acetate
pentachlorobenzyl alcohol
di-(5-chloro-2-hydroxyphenyl)-methane
phenyl-(5-chloro-2-hydroxyphenyl)-methane
N-trichloromethylthiotetrahydrophthalimide
N-trichloromethylthiophthalimide
N-fluorodichloromethylthiophthalimide
N-(1,1,2,2-tetrachloroethylthio)-tetrahydrophthalimide
2-heptadecyl-2-imidazoline acetate 2,4-dichloro-6-(o-chloroanilino)-s-triazine
diethylphthalimidophosphorothionate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
quinoxaline-2,3-cycl.-trithiocarbonate
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
1-(1,2,4-triazolyl-1′)-[4′-chlorophenoxy)]-3,3-dimethylbutan-2-one
1-(1-imidazoyl)-2-allyloxy-2-(2,4-dichlorophenyl)-ethane
2-(O,O-diethylthionophosphoryl)-5-methyl-6-carbethoxypyrazolo-(1,5a)-pyrimidine
pyridine-2-thiol-1-oxide
8-hydroxyquinoline and its copper salt
5,5-dimethyl-3-(3,5-dichlorophenyl)-2,4-dioxo-1,3-oxazolidine
5-methyl-5-vinyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
dodecylguanidine acetate
3-[2-(3,5-dimethyl-2-oxycyclohexyl)-2-hydroxyethyl]-glutarimide hexachlorobenzene
N-dichlorofluoromethylthio-N,N′-dimethyl-N-phenylsulfuric acid diamide
N-dichlorofluoromethylthis-N-methyl-N′-methyl-N-phenylsulfuric acid diamide
2,4,5,6-tetrachloroisophthalonitrile
1-(3,4-dichloroanilino)-1-formylamino-2,2,2-trichloroethane
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzene diazosodium sulfonate
1-chloro-2-nitropropane
polychloronitrobenzenes such as pentachloronitrobenzene
methyl isocyanate
triphenyl tin acetate
fungicidal antibiotics, e.g., griseofulvin and kasugamycin
mercaptobenzothiazole
methyl-N-(2,6-dimethylphenyl)-N-(2-furoyl)-alaninate
methyl-N-(2,6-dimethylphenyl)-N-(2-methoxyacetyl)-alaninate
2-cyano-N-[(ethylamino)-carbonyl]-2-(methoximino)-acetamide
β-(4-chlorophenxy)-α-(1,1-dimethyl)-1H-1,2,4-triazole-1-ethanol
benzisothiazolone
tetrafluorodichloroacetone
1-phenylthiosemicarbazide
aluminum complex of N′-hydroxy-N-cyclohexyldiazenium oxide and the corresponding sodium and potassium complexes
Bordeaux mixture
nickel-containing compounds, and sulfur.

These agents may be added to the fungicides according to the invention in a weight ratio of from 1:10 to 10:1. If desired, they need not be added until immediately before use (tankmix).

The following examples demonstrate the fungicidal action of the new compounds. The following 3 prior art compounds were used for comparison purposes:

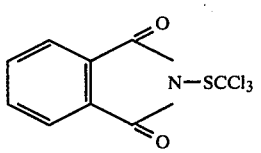

compound A

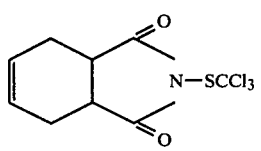

compound B

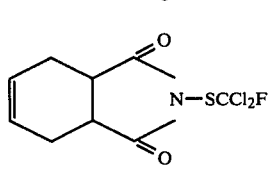

compound C

EXAMPLE 2

The active ingredients are added to a nutrient solution ideally suited for promoting the growth of the fungus *Aspergillus niger*, in amounts of 100, 50, 25, 10, 5 and 1 parts by weight per million parts of nutrient solution. 20 ml lots of the nutrient solution treated in this manner are placed in 100 ml glass flasks and inoculated with 0.3 mg of Aspergillus spores. The flasks are incubated at 36° C. for 120 hours, and the extent of fungus spread—predominantly on the surface of the nutrient solution—is then assessed.

0 = no fungus growth, graduated down to
5 = uncontrolled fungus growth (surface of nutrient solution completely covered by fungus)

| Active ingredient | Parts of active ingredient per million parts of nutrient solution | | | | | |
|---|---|---|---|---|---|---|
| | 100 | 50 | 25 | 10 | 5 | 1 |
| 4 | 0 | 0 | 0 | 0 | 0 | 0 |
| 6 | 0 | 0 | 0 | 0 | 0 | 0 |
| 8 | 0 | 0 | 0 | 0 | 0 | 0 |
| 10 | 0 | 0 | 0 | 0 | 0 | 0 |
| 12 | 0 | 0 | 0 | 0 | 1 | 2 |
| 26 | 0 | 0 | 0 | 0 | 0 | 1 |
| 28 | 0 | 0 | 0 | 0 | 0 | 1 |
| 30 | 0 | 0 | 0 | 0 | 0 | 0 |
| 32 | 0 | 0 | 0 | 0 | 0 | 3 |
| 34 | 0 | 0 | 0 | 0 | 2 | 4 |
| 46 | 0 | 0 | 0 | 0 | 0 | 0 |
| 48 | 0 | 0 | 0 | 0 | 0 | 0 |
| (A) | 0 | 0 | 2 | 4 | 4 | 5 |
| (B) prior art | 0 | 1 | 3 | 4 | 4 | 5 |
| (C) | 0 | 0 | 0 | 1 | 3 | 4 |

EXAMPLES 3

100 g samples of pea seeds of the "Senator" variety are carefully shaken for about 5 minutes in glass bottles with 300 mg (=0.3 wt%) of seed disinfectant formulations containing (dry basis) 40% of active ingredient. Subsequently, 100 seeds are sown 3 cm deep and 3 to 5 cm apart in seed boxes in a compost naturally and heavily infested with the fungi Pythium spec., Aphanomyces spec. and *Fusarium oxysporum*. The boxes are set up in the greenhouse at from 17° to 20° C. The number of healthy pea plants is determined after 21 days.

| Active ingredient | Percentage of healthy plants after 21 days in compost |
| --- | --- |
| 1 | 90 |
| 3 | 92 |
| 4 | 93 |
| 5 | 80 |
| 6 | 84 |
| 7 | 96 |
| 8 | 92 |
| 9 | 95 |
| 10 | 91 |
| 11 | 82 |
| 12 | 86 |
| 26 | 95 |
| 27 | 90 |
| 28 | 86 |
| 29 | 88 |
| 30 | 92 |
| 31 | 94 |
| 32 | 93 |
| 45 | 88 |
| 46 | 84 |
| 47 | 93 |
| 48 | 95 |
| B (prior art) | 65 |
| control (untreated) | 15 |
| control (sterilized compost) | 95 |

EXAMPLE 4

Filter paper discs 13 mm in diameter and 1 mm thick are impregnated with 0.2 ml of solutions each containing 400 parts of active ingredient per million parts of solution (ppm). The discs are then placed on a 5% malt extract agar in glass dishes (with lid) which have previously been inoculated with spores of the fungus *Pullularia pullulans*. The dishes are then incubated for 3 days at from 22° to 24° C. After this time, the fungi in the control dishes have spread very well; the fungicidal action of the active ingredients is assessed in the following manner from the fungus-free zones (halos) which have formed round the filter − no halo (no fungicidal action)
\+ halo less than 1 mm in width (slight fungicidal action)
++ average halo from 1 to 5 mm in width (good fungicidal action)
+++ halo wider than 5 mm (excellent fungicidal action)

| Active ingredient | Assessment of fungicidal action (halo assessment) |
| --- | --- |
| 1 | +++ |
| 2 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |

-continued

− no halo (no fungicidal action)
\+ halo less than 1 mm in width (slight fungicidal action)
++ average halo from 1 to 5 mm in width (good fungicidal action)
+++ halo wider than 5 mm (excellent fungicidal action)

| Active ingredient | Assessment of fungicidal action (halo assessment) |
| --- | --- |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 45 | +++ |
| 46 | +++ |
| 47 | +++ |
| 48 | +++ |
| (A) | ++ |
| (B) prior art | + |
| (C) | ++ |
| control (untreated) | − |

EXAMPLE 5

90 parts by weight of compound 1 is mixed with 10 parts by weight of N-methyl-α-pyrrolidone. A mixture is obtained which is suitable for application in the form of very fine drops.

EXAMPLE 6

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 9

3 parts by weight of compound 3 is intimately mixed with 97 parts by weight of particulate kaolin. A dust is obtained containing 3% by weight of the active ingredient.

EXAMPLE 10

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

40 parts by weight of compound 1 is intimately mixed with 10 parts of the sodium salt of a phenolsulfonic acid-urea-formaldehyde condensate, 2 parts of silica gel and 48 parts of water. A stable aqueous dispersion is obtained. Dilution in 100,000 parts by weight of water gives an aqueous dispersion containing 0.04 wt% of active ingredient.

EXAMPLE 12

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An N-sulfenylated formanilide of the formula

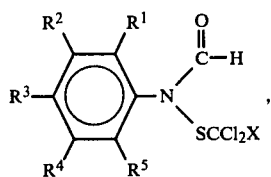

where X denotes fluorine or chlorine, and $R^1$, $R^2$, $R^3$, $R^4$ and $R^5$ are identical or different and each denotes hydrogen, halogen, nitro, linear or branched, unsubstituted or halogen-substituted alkyl or alkoxy of 1 to 4 carbon atoms, or —CN or —$COR^6$, $R^6$ denoting linear or branched alkoxy of 1 to 6 carbon atoms or dialkylamino, the alkyls being linear or branched and of 1 to 4 carbon atoms, or $R^6$ denoting N-alkyl-N-arylamino, alkyl being of from 1 to 4 carbon atoms and aryl being unsubstituted or substituted by halogen or alkyl.

2. A method of combating fungi which comprises applying to the fungi or the objects to be protected against fungus attack with a fungicially effective amount of a formanilide of the formula

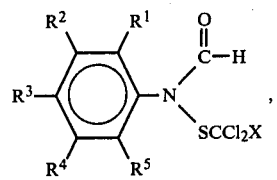

where X denotes fluorine or chlorine, and $R^1$, $R^2$, $R^3$, $R^4$ and $R^5$ are identical or different and each denotes hydrogen, halogen, nitro, linear or branched, unsubstituted or halogen-substituted alkyl or alkoxy of 1 to 4 carbon atoms, or —CN or —$COR^6$, $R^6$ denoting linear or branched alkoxy of 1 to 6 carbon atoms or dialkylamino, the alkyls being linear or branched and of 1 to 4 carbon atoms or $R^6$ denoting N-alkyl-N-arylamino, alkyl being of from 1 to 4 carbon atoms and aryl being unsubstituted or substituted by halogen or alkyl.

3. An N-sulfenylated formanilide selected from the group consisting of N-(trichloromethylsulfenyl)-2-fluoroformanilide, N-(fluorodichloromethylsulfenyl)-4-methylformanilide, N-(trichloromethylsulfenyl)-2,6-difluoroformanilide, N-(fluorodichloromethylsulfenyl)-2,6-difluoroformanilide, N-(trichloromethylsulfenyl)-3-chloro-4-fluoroformanilide, and N-(fluorodichloromethylsulfenyl)-3-chloro-4-fluoroformanilide.

* * * * *